United States Patent [19]

Yearian

[11] 4,186,195
[45] Jan. 29, 1980

[54] VIRUS INSECTICIDE COMPOSITION

[75] Inventor: William C. Yearian, Fayetteville, Ark.

[73] Assignee: Sandoz, Inc., E. Hanover, N.J.

[21] Appl. No.: 923,292

[22] Filed: Jul. 10, 1978

Related U.S. Application Data

[63] Continuation of Ser. No. 862,364, Dec. 20, 1977, abandoned, which is a continuation of Ser. No. 705,157, Jul. 14, 1976, abandoned.

[51] Int. Cl.$^2$ .......................... A01N 9/02; A01N 9/20; A01N 15/00
[52] U.S. Cl. ....................................... 424/93; 424/326
[58] Field of Search ................................. 424/93, 326

[56] References Cited

U.S. PATENT DOCUMENTS

| | | | |
|---|---|---|---|
| 3,502,720 | 3/1970 | Unna et al. | 424/326 X |
| 3,541,203 | 11/1970 | Fogle et al. | 424/17 |
| 3,639,578 | 2/1972 | Batzer | 424/93 |
| 3,937,813 | 2/1976 | Clarke, Jr. | 424/93 |

FOREIGN PATENT DOCUMENTS 962943  2/1975  Canada .

*Primary Examiner*—Allen J. Robinson
*Attorney, Agent, or Firm*—Gerald D. Sharkin; Richard E. Vila

[57] ABSTRACT

Improved insecticides are provided by compositions comprising a Heliothis virus in combination with chlordimeform.

17 Claims, No Drawings

VIRUS INSECTICIDE COMPOSITION

This is a continuation, of application Ser. No. 862,364, filed Dec. 20, 1977, which in turn is a continuation, of application Ser. No. 705,157, filed July 14, 1976, now both abandoned.

A major means of reducing crop losses by insect pests has been the use of chemical insecticides. In the past few years, however, interest has grown in the use of biological means of controlling insect pests. A factor in this increasing interest in biological pest control is the increasing awareness of the potentially adverse side effects of broad spectrum chemical pesticides. A principal area of biological control is the employment of bacteria and viruses that are pathogenic for a particular insect pest. These insecticides can be manufactured in advance, stored in concentrated form and applied in relatively small quantities to selected areas at the most appropriate time.

Virus insecticides, and in particular those that contain proteinaceous inclusion bodies with occluded virions, have been reported for a variety of harmful insects including the cotton bollworm, the tobacco budworm, the cabbage looper, the fall armyworm, the beet armyworm, the alfalfa caterpillar and the like. Inclusion bodies with occluded virions, and the production and use of virus insecticides containing them are described, inter alia, in Steinhaus and Thompson, Preliminary Field Tests Using a Polyhedrosis Virus to Control the Alfalfa Caterpillar, Journal of Economic Entomology, Vol. 42, No. 2, pp. 301–305, (April 1949); Ignoffo, Production and Virulence of a Nuclear-Polyhedrosis Virus from Larvae of *Trichoplusia ni* (Hubner) Reared on a Semi-synthetic Diet, Journal of Insect Pathology, 6, pp. 318–326 (1964); Ignoffo, The Nuclear-Polyhedrosis Virus of *Heliothis zea* (Boddie) and *Heliothis virescens* (Fabricius), Journal of Invertebrate Pathology, 7, No. 2, pp. 209–216 and 217–226 (June, 1965); Ignoffo, Possibilities of Mass-Producing Insect Pathogens, Internat. Colloq. Insect Pathol. Netherlands, pp. 91–117 (1967); Ignoffo, Viruses-Living Insecticides, Current Topics in Microbiology and Immunology, Vol. 42, pp. 129–167 (1968); and U.S. Pat. No. 3,639,578.

Viruses of the family or complex Heliothis are useful in combatting insects of the family or complex Heliothis, particularly in the various larvae stages. Recently, a virus of *Heliothis zea* has been made available commercially in the United States under the registered trademark ELCAR. While such viruses embody the features desired for a virus insecticide, there is considerable room for improvement in a number of areas of the technology including potency, stability, adjuvant systems and ability to control unusually heavy insect populations at rates which are judged economical. Many of these factors are interrelated, i.e. an improvement in one factor such as adjuvant systems can effect an improvement in another such as potency, but independent approaches to the improvement of these factors are available. For example, it is known to experiment with combinations of two insecticides in the hope of providing various improvements but such attempts to the extent providing significant improvement from an activity standpoint are usually unsuccessful, and especially in terms of providing economically practical benefits.

The compound N'-(4-chloro-o-tolyl)-N,N-dimethylformamide, in free base or acid addition salt form, known generically as chlordimeform, is a commercially available insecticide. Chlordimeform is known to be active against the larvae of lepidopterus and to also exhibit ovicidal effects. The disadvantages of chlordimeform include those now commonly associated with many chemical insecticides, i.e. environmental uncertainty and insect tolerance that tends to lead toward less economical application rates and increased environmental concern.

It has now been found that certain compositions containing both Heliothis virus and chlordimeform provide a combination insecticide permitting control of Heliothis pests that exceeds the control obtainable with the same total amounts of the individual active components.

The compositions provided by the present invention comprise 1 part by weight chlordimeform and the equivalent of from 0.25 to 2.0 parts, preferably 0.5 to 1.5 parts, more preferably 0.6 to 1.25 part, by weight of a Heliothis virus formulation having an $LD_{50}$ against the first instar *Heliothis zea* larvae of 0.1 micrograms per milliliter as determined in accordance with the standard assay procedure hereinafter described.

Further in accordance with the invention the compositions above provided are employed in the combatting of pests of the family Heliothis in agricultural crops containing the same by applying such a composition to the crop in an amount sufficient to provide from 0.08 to 0.25 pound, preferably 0.1 to 0.2 pound, and more preferably 0.1 to 0.16 pound, of chlordimeform per acre.

In defining the present invention reference has been made to Heliothis virus formulations having, on a weight basis, a specified toxicity or $LD_{50}$ against the first instar *Heliothis zea* in accordance with a standard assay method, and the amounts to be used in the invention are referenced to equivalent amounts of a virus formulation having such specified toxicity. This has been done to ensure preciseness in determining the actual amount of virus employed in terms of its activity. Hence, unlike chemical insecticides, it is difficult to weigh the virions that actually constitute the active portion of a virus and other methods such as counting the virions or inclusion bodies or determining the number of larvel equivalents are equally impractical and/or imprecise for a number of reasons such as the possible presence of ineffective or dead virions and variations in manufacturing techniques that directly influence the number of virions or inclusion bodies in each larvae. Accordingly, it is deemed more precise to refer to an amount of virus insecticide having an arbitrary (but commercially obtainable) standard activity or toxicity by a known and standard assay. For example, a 1 gram amount of a virus formulation having an $LD_{50}$ of 0.1 would be equivalent to a 2 gram amount of a virus formulation having an $LD_{50}$ of 0.2 in the assay and so forth. The term "formulation" as used in connection with the Heliothis virus is meant to reflect and contemplate the fact that the actual virus, i.e. virions or inclusion bodies, are, except possibly for limited periods during certain manufacturing stages, not tangibly available or procedurally suitable for combination with chlordimeform in such pure virus forms per se, but rather are isolated and tangibly available only when physically combined with at least one other substance. While such substance may be represented by larvae cell debris or various processing mediums at the minimum, the term is also designed to include and preferably represent the more practical forms a virus insecticide such as those in which the virions or inclusion bodies are combined with inert carriers which may be solid or liquid, and especially the storable and saleable forms, e.g. wettable powders such as now available under the Trademark ELCAR, liquid concentrates (generally nonaqueous) and the like. The term is also intended to include more dilute forms such as those used in field applications and obtained, for example, by mixing a wettable powder with water. Hence, the term "Heliothis virus formulation" is generally intended to mean any tangible combination of Heliothis virus virions or inclusion bodies with another substance essentially of a non-delecterious or inert nature, but the preferred forms thereof are the storable and saleable concentrates that typically contain 0.1 to 2.0 by weight virions, desirably inclusion bodies, in combination with an inert carrier and such other optional or supportive ingredients as may be desired such as stabilizers, wetting agents and the like. As used herein, and unless otherwise clearly indicated by separate delineation or clear meaning of the text, the term "carrier" is meant to include materials that also may be referred to or recognized by those skilled in the art as adjuvants.

The compositions of the present invention may be prepared in any of a variety of ways that are evident to and within the skill of those in the art, and may be embodied in various forms such as powders, dust, liquid concentrates and sprays and the like. For example, the commercially available insecticides involving a wettable powder containing 0.4% inclusion bodies of *Heliothis zea* NPV and 99.6% inert ingredients and a technical concentrate of chlordimeform containing 95–98% active ingredient may be combined in the indicated proportions in a container and simply mixed together. The resulting concentrate form of the compositions of the invention may be placed on the surface of water in a spray tank and agitation applied to provide a dilute sprayable composition. Alternately, the individual insecticides may be separately mixed with water by agitation in the spray tank or both may be mixed with water in separate tanks and then combined in a single spray tank with agitation. All such procedures are suitable. Dilute aqueous forms for spray applications typically contain from 94 to 99.9 percent by weight water. In general, dilute forms for application purposes may contain from about 0.05 percent to 4.0 percent by weight chlordimeform, preferably 0.08 percent to 3.5 percent, by total weight of the composition.

The compositions of the invention in dilute application form may be employed in the combatting of pests of the family or complex Heliothis in any of the variety of agricultural crops in which they are found. Such crops include without limitation, cotton, tobacco, tomatoes and the cole crops. A crop of particular interest and constituting a preferred embodiment of the invention is cotton. The compositions are particularly useful in combatting the Heliothis pests in the pre-adult stages, particularly the pre-pupae stages, and are desirably applied upon the first recognition of the deposition of eggs or appearance of the first instar larvae. The Heliothis species *Heliothis zea, Heliothis viriscens,* and *Heliothis armigera* are important pests affecting crop production and the treatment thereof either individually or in combined populations, particularly the first two such secies in the United States, constitutes preferred ebodiments of the invention. Such species may reside in cotton and an especially preferred embodiment of the invention is therefore the combatting of populations of one or more such ecies in cotton, and particularly one or both of *Heliothis zea* and *Heliothis viriscens* in cotton in the United States. While no certain explanation can be given for the beneficial results provided by the invention, it is believed that chlordimeform may also result in larvae that are more susceptible to the virus disease.

Other pesticides such as insecticides, may be applied concurrent with or included in the compositions of this invention as desired, provided that such are suitably compatible with the virus insecticide - chlordimeform constituents of this invention. For example, in treating cotton for infestations of the cotton bollworm and/or the tobacco budworm it is at times advantageous to include azinphosmethyl as treatment against the boll weevil.

Chlordimeform is disclosed in U.S. Pat. Nos. 3,378,437 and 3,502,720, and is commercially available. The production of Heliothis virus for insecticide purposes is well known and need not be described. However, the formulation of the virus into a practical or commercially acceptable insecticide is not a simple matter in view of a number of considerations including particularly the susceptibility of the virus to degradation from heat and light and accordingly the stability and potency of the insecticide. Accordingly, the formulation of the virus plays an importent part in the realization of a practical virus insecticide. In the composition of the invention a preferred Heliothis virus formulation is represented by the commercial product ELCAR which essentially comprises fine particles obtained by spray drying and containing the virus in the form of inclusion bodies encapsulated in a matrix consisting essentially of 56 percent by weight defatted soybean powder (K-Soy), 30 percent Attapulgus clay (ATTA-CLAY) and 6 percent by weight potassium dihydrogen phosphate, the balance being the inclusion bodies and larvae cell matter. Such spray dried particles may be prepared in accordance with co-pending but now abandon U.S. patent application Ser. No. 596,986, filed July 18, 1975 in the name of Tsuong R. Shieh and Martin H. Rogoff, the disclosure of which is hereby incorporated herein by reference. *Heliothis zea* is the preferred Heliothis virus source for use in the invention.

The following examples are illustrative of the compositions and methods of use of this invention. The virus used in the examples is a wettable powder (WP) which is essentially ELCAR as previously described and having an average $LD_{50}$ of 0.10. The "Adjuvant" employed in the following examples is a water dispensible liquid that is a blend of crude cottonseed oil (50 weight percent), soybean protein flour (K-Soy-45 weight percent) and a wetting agent (5 weight percent-ATLOX 775) and prepared by first mixing the cottonseed oil with the wetting agent following by mixing the resulting liquid with the soybean flour. The above-mentioned Adjuvant does not form a part of this invention, but may advantageously be used therewith. The chlordimeform employed is a 96–98% technical concentrate available under the trademark FUNDAL.

EXAMPLE 1

Employing standard test procedures on cotton involving 0.1 acre test plots (4 replicates) and a total of 9 applications over a period of one and one half months from mid July to late August, a series of insecticides are evaluated for effect against a combined but varying *Heliothis zea* and *Heliothis viriscens* population and effect on yield. All applications are in the form of an aqueous suspension from a tank sprayer applied at a rate of 10 gallons per acre. Amounts of insecticide and the results are given in the following table A.

TABLE A

| Test No. | Material | Amt./A | 4 1 Mean No. Heliothis Eggs/A ($\times 10^3$) | 1 Mean No. Heliothis Larva/A ($\times 10^3$) | 1 Mean No. squares/ A ($\times 10^3$) | 1 Mean No. Heliothis Damaged Squares/A ($\times 10^3$) | 1 Mean % Heliothis Damaged Squares/A ($\times 10^3$) | 1 Mean No. Bolls/A ($\times 10^3$) | 1 Mean No. Heliothis Damaged Bolls/A ($\times 10^3$) | 1 Mean % Heliothis Damaged Bolls | 2 3 Mean Yield/A (lbs. seed cotton) |
|---|---|---|---|---|---|---|---|---|---|---|---|
| 1 | Virus | 15 g. | 5.0 | 4.7 | 136.4 | 15.9 | 11.6 | 22.7 | 2.6 | 11.4 | 504.4 |
| 2 | Virus | 30 g. | 5.3 | 5.1 | 106.4 | 13.9 | 13.1 | 20.4 | 0.7 | 3.4 | 643.3 |
| 3 | Virus | 60 g. | 4.8 | 4.6 | 125.9 | 13.3 | 10.6 | 25.6 | 2.0 | 7.8 | 575.9 |
| 4 | Virus | 120 g. | 4.8 | 2.7 | 108.2 | 9.9 | 9.1 | 36.2 | 1.1 | 3.0 | 617.5 |
| 5 | Virus + Chlordimeform | 15 g. 0.125 lb. | 4.9 | 2.5 | 104.1 | 11.4 | 11.0 | 26.4 | 0.8 | 3.0 | 540.7 |
| 6 | Virus + Chlordimeform | 30 g. 0.125 lb. | 4.0 | 3.5 | 143.1 | 11.8 | 8.4 | 34.8 | 1.1 | 3.0 | 780.9 |
| 7 | Virus + Chlordimeform | 60 g. 0.125 lb. | 4.8 | 3.9 | 134.0 | 10.2 | 7.5 | 32.0 | 1.3 | 4.0 | 862.4 |
| 8 | Chlordimeform | 0.125 lb. | 4.0 | 3.7 | 154.0 | 11.9 | 7.7 | 26.8 | 2.0 | 7.3 | 633.7 |
| 9 | Control (untreated) | — | 3.7 | 4.8 | 130.1 | 15.1 | 11.6 | 20.5 | 2.4 | 11.3 | 356.8 |
| 10 | Virus Chlordimeform Adjuvant | 60 g. 0.125 lb. 1 quart | | | | | | | | | >900 |

EXAMPLE 2

Tests were made in Mississippi on protection against damage to growing cotton by Heliothis species. In the tests the virus insecticide was used as a wettable powder. A test plot of 5 similar rows, 50 feet long each, (4 replicates) of growing cotton of variety ST 603 was treated thirteen times over a period of two months during the growing season (late July to late September; at about 5-day intervals). The insecticides were applied by tractor-drawn sprayer (TX nozzle) at a rate of 15 gallons/acre. Egg counts were made (reported as mean egg counts per 40 terminal leaves per treatment); % larval infestation of bolls was recorded, and yield of seed cotton determined. The results are shown in Table B below:

Table B

| Test No. | Test Material | Amount/ Acre | Mean Egg Counts | % Larval Infestation | Yield Seed Cotton lb./A |
|---|---|---|---|---|---|
| 1 | Virus | 30 g. | 34.90 | 7.75 | 1684.97 |
| 2 | Virus | 60 g. | 36.60 | 5.3 | 1561.63 |
| 3 | Virus | 120 g. | 27.70 | 7.83 | 1499.45 |
| 4 | Virus + Chlordime- form | 60 g. + 0.25 lb. | 19.30 | 5.0 | 2183.38 |
| 5 | Control | — | 66.20 | 15.1 | 1389.83 |

EXAMPLE 3

Tests carried out in Louisiana under similar test conditions to those described in Example 3, except that the cotton variety was DPL 16, 8 rows; 50 ft. long; 4 replications, and 10 applications made over a period of 7 weeks (Aug. to Sept.) gave the results shown in Table C:

Table C

| Test No. | Test Material | Amount | Average % Heliothis Squares | Average % Damaged Bolls | Yield Seed Cotton lb/A. |
|---|---|---|---|---|---|
| 1 | Virus | 30 g. | 8.46 | 8.25 | 1470 |
| 2 | Virus | 60 g. | 11.96 | 11.5 | 1660 |
| 3 | Virus | 120 g. | 12.04 | 7.0 | 1542 |
| 4 | Virus + Chlordime- form | 60 g. + 0.25 lb. | 5.75 | 4.0 | 1830 |

EXAMPLE 4

In tests carried out in Mississippi under conditions similar to those described in Example 3, except that the test plot consisted of 8 rows; 170 ft. long each, 28 inches between rows; 4 replicates; cotton variety ST 213 and applied 8 times within a period of about 5 weeks (Aug. to Sept). gave the results shown in Table D wherein a 33% turn out of lint is assumed to arrive at the lint/acre yield figures:

Table D

| Test No. | Test Material | Amount | Seed Cotton/ Acre | Lint/ Acre |
|---|---|---|---|---|
| 1 | Virus | 30 g. | 2858 | 714 |
| 2 | Virus | 60 g. | 2790 | 697 |
| 3 | Virus | 120 g. | 2962 | 740 |
| 4 | Virus + Chlordime- form | 60 g. + 0.25 lb. | 2872 | 718 |
| 5 | Control | — | 2672 | 668 |

EXAMPLE 5

In tests carried out in Texas under conditions similar to those described in Example 2 on a 0.1 acre plot (40 inch spacing; 4 replicates) on Stonville 213 cotton, the results shown in Table E were obtained:

Table E

| Test No. | Test Material | Amt./A | % eggs* | % larvae* | % larvae in square | % larval damage/ square | % damage bolls | Yield lbs. lint/A |
|---|---|---|---|---|---|---|---|---|
| 1 | Virus | 30 g | 28a | 13bc | 6b | 14ab | 18a | 217a |
| 2 | Virus | 60 g | 34cd | 16bc | 5ab | 13ab | 15a | 250ab |
| 3 | Virus | 120 g | 33bcd | 15bc | 5ab | 14ab | 18a | 221a |

Table E-continued

| Test No. | Test Material | Amt./A | % eggs* | % larvae* | % larvae in square | % larval damage/ square | % damage bolls | Yield lbs. lint/A |
|---|---|---|---|---|---|---|---|---|
| 4 | Virus + Chlordimeform | 60 g + 0.25 lb. | 30abc | 7a | 3ab | 10ab | 9a | 421bc |
| 5 | Control | — | 35d | 17c | 9c | 20c | 32b | 150a |

Notes:
1. Boll weevil infestations were prevented by early season control with azinphosmethyl
2. Means with different letters are significantly different at the 0.05 level by Duncan's multiple range test.
3. * = in terminal leaves.

The measurement of insecticidal activity or potency as used and referred to in this specification is based on determination of the $LD_{50}$ value reported in micrograms per ml. ($\gamma$/ml.) of diet required to provide a level dose for 50 percent of the first instar larvae grown at a temperature of 30° C. The method is basically described in Insect Pathology; 6, 737–45 (1965) in connection with *Trichopusia ni* NPV potency estimation. The nutrient employed in such test has the following composition:

| Ingredient: | | Amount |
|---|---|---|
| Distilled water | ml | 3,100 |
| Methyl parahydroxybenzoate (15% w./v. in 95% ethyl alcohol) | ml | 36 |
| Choline chloride (0.1 g./ml. water) | ml | 36 |
| Potassium hydroxide, 4 molar | ml | 18 |
| Formalin (0.1 g./ml.) | ml | 15 |
| Vitamin stock[1] | ml | 6 |
| Casein | g | 126 |
| Sucrose | g | 126 |
| Wheat germ | g | 108 |
| Agar | g | 90 |
| Wesson's salts | g | 36 |
| Alphacel | g | 18 |
| Ascorbic acid | g | 15 |
| Antibiotic(chlortetracycline, kanamycin) | | |

[1]600 mg. niacin, 600 mg. calcium pantothenate, 300 mg. riboflavin, 150 mg. each of thiamin, pyridoxin and folic acid, 12 mg. biotin, nd 1.2 mg. of vitamin B-12 in 100 ml. distilled water. Preparation of nutrient is described in Journal of Invertebrate Pathology, 7, No. 2, pp. 217-226 (June 1965).

What is claimed is:

1. An insecticidal composition for combatting pests of the family Heliothis comprising 1 part by weight N'-(4-chloro-o-tolyl)-N,N-dimethylformamidine and the equivalent of from 0.5 to 1.5 parts by weight of a Heliothis virus formulation having an $LD_{50}$ against the first instar Heliothis zea larvae of 0.1 micrograms per milliliter.

2. The insecticidal composition in accordance with claim 1 in which the amount of Heliothis virus formulation is equivalent to from 0.6 to 1.25 parts by weight.

3. The insecticidal composition in accordance with claim 1 in which the Heliothis virus is the *Heliothis zea* virus.

4. The insecticidal composition in accordance with claim 2 in sprayable application form in which the Heliothis virus is the *Heliothis zea* virus and in which water is present as a carrier in an amount constituting from 94 to 99.9 percent by weight of the total composition.

5. The method of combatting pests of the family Heliothis in an agricultural crop infested with the same comprising applying to the crop a composition of claim 1 in an amount sufficient to provide from 0.08 to 0.25 pounds of N'-(4-chloro-o-tolyl)-N,N-dimethylformamidine per acre.

6. The method of combatting pests of the family Heliothis in an agricultural crop infested with the same comprising applying to the crop a composition of claim 2 in an amount sufficient to provide from 0.08 to 0.25 pounds of N'-(4-chloro-o-tolyl)-N,N-dimethylformamide per acre.

7. The method of claim 5 in which the composition is applied in an amount sufficient to provide from 0.1 to 0.2 pounds of N'-(4-chloro-o-tolyl)-N,N-dimethylformamide per acre.

8. The method of claim 6 in which the composition is applied in an amount sufficient to provide from 0.1 to 0.2 pounds of N'-(4-chloro-o-tolyl)-N,N-dimethylformamide per acre.

9. The method of claim 5 in which the crop is cotton.

10. The method of claim 6 in which the crop is cotton.

11. The method of claim 8 in which the crop is cotton.

12. The method of claim 5 in which the Heliothis pests are selected from the group consisting of *Heliothis zea, Heliothis virescens* and both said species.

13. The method of claim 9 in which the Heliothis pests are selected from the group consisting of *Heliothis zea, Heliothis virescens* and both said species.

14. The method of claim 11 in which the Heliothis pests are selected from the group consisting of *Heliothis zea, Heliothis virescens* and both said species.

15. The method of claim 5 in which the Heliothis virus is the *Heliothis zea* virus.

16. The method of claim 14 in which the *Heliothis zea* virus is the *Heliothis zea* virus.

17. The method of claim 5 in which the crop is selected from the group consisting of cotton, tobacco, tomatoes and cole crops.

* * * * *